(12) United States Patent  (10) Patent No.: US 8,754,154 B2
Dave et al.  (45) Date of Patent: Jun. 17, 2014

(54) TRIAZINE COMPOUNDS CONTAINING PHOSPHOROUS AS FLAME RETARDANTS

(75) Inventors: Trupti Dave, Zwingenberg (DE); Wolfgang Wehner, Zwingenberg (DE)

(73) Assignee: Catena Additives GmbH & Co. KG, Alsbach-Hahnlein (DE)

( * ) Notice: Subject to any disclaimer, the term of this patent is extended or adjusted under 35 U.S.C. 154(b) by 427 days.

(21) Appl. No.: 12/671,625

(22) PCT Filed: Jul. 16, 2008

(86) PCT No.: PCT/EP2008/005795
§ 371 (c)(1),
(2), (4) Date: Feb. 1, 2010

(87) PCT Pub. No.: WO2009/015772
PCT Pub. Date: Feb. 5, 2009

(65) Prior Publication Data
US 2011/0245383 A1    Oct. 6, 2011

(30) Foreign Application Priority Data
Aug. 1, 2007 (DE) .......................... 10 2007 036 465

(51) Int. Cl.
C08K 5/34 (2006.01)
(52) U.S. Cl.
USPC ........... 524/100; 524/101; 524/405; 524/430; 524/437; 524/442; 528/395
(58) Field of Classification Search
USPC ................. 524/100, 101, 405, 430, 437, 442; 528/395
See application file for complete search history.

(56) References Cited

U.S. PATENT DOCUMENTS 6,369,137 B2 * 4/2002 Kersjes et al. ................ 524/100

FOREIGN PATENT DOCUMENTS

| DE | 3622840 A1 | 1/1987 |
|---|---|---|
| EP | 0393421 A3 | 10/1990 |
| EP | 1095975 A2 | 5/2001 |
| EP | 1116773 A1 | 7/2001 |
| GB | 1386746 | 3/1975 |
| JP | WO 9744377 | * 11/1997 |
| JP | 2007-070615 | 3/2007 |
| WO | WO-2005052031 | 6/2005 |
| WO | WO 2006/092363 | 9/2006 |

OTHER PUBLICATIONS

USPTO structure search, Jul. 2012.*
XP002649572—Database WPI Week 200745, Thomson Scientific, London, GB; AN 2007-461808.

* cited by examiner

Primary Examiner — Gregory Listvoyb
(74) Attorney, Agent, or Firm — Klauber & Jackson LLC

(57) ABSTRACT

The present invention relates to phosphorus-containing triazine compounds of the formula (I) and (III) and to the polymers obtainable from the water-eliminating polycondensation of a compound of the formula (II), and to the use thereof as flame retardants.

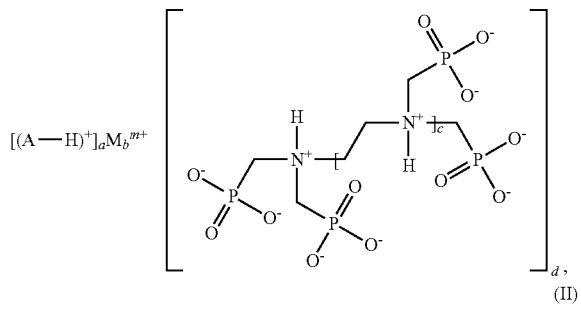

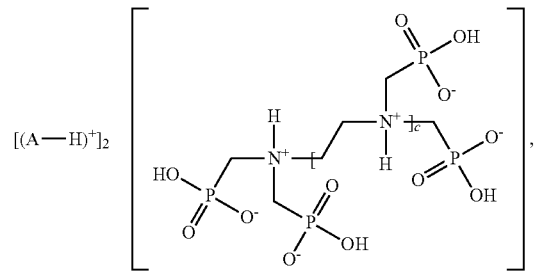

$[(A-H)^+]_m[M^{m+}(HPO_4^{2-})_m]$   (III-1), $[(A-H)^+]_m[M^{m+}(P_2O_7^{4-})_{m/2}]$   (III-2).

9 Claims, 4 Drawing Sheets

TRIAZINE COMPOUNDS CONTAINING PHOSPHOROUS AS FLAME RETARDANTS

CROSS REFERENCE TO RELATED APPLICATIONS

The present application is a National Stage Application claiming the priority of co-pending PCT Application No. PCT/EP2008/005795 filed Jul. 16, 2008, which in turn, claims priority from German Application Serial No. 10 2007 036 465.4 filed Aug. 1, 2007. Applicants claim the benefits of 35 U.S.C. §120 as to the PCT application and priority under 35 U.S.C. §119 as to the said German application, and the entire disclosures of both applications are incorporated herein by reference in their entireties.

The present invention relates to phosphorous-containing triazine compounds, to the use thereof as flame retardants and to the polymers comprising the compounds.

Metal phosphonates are known per se or in combination with other components for a large number of thermoplastic polymers.

Nitrogen-containing flame retardants, especially based on melamine, have been known for some time, and some are also commercially available. Some of these melamine compounds also contain phosphorous.

U.S. Pat. No. 5,684,071 describes, in general terms, melamine salts of nitrilo(amino)trimethane-phosphonic acid (NTMPA) as flame retardants. Trimelamine- and hexamelamine-NTMPA salt are described in EP-A 1 116 773. EP-A 1 116 772, in contrast, describes trimagnesium, tricalcium and trizinc nitrilo(amino)trimethanephosphonate as flame retardant components.

In spite of the numerous flame retardants known in the prior art, there is still a need for flame retardants with optimized properties and improved environmental compatibility.

SUMMARY

It is therefore an object of the present invention to provide such flame retardants.

The object is achieved by a compound of the formula (I)

$$[(A-H)^+]_a M_b^{m+} \left[ \text{structure} \right]_d \quad (I)$$

where
$(A-H)^+$ is a radical of the formula (IV)

$$\text{(IV)}$$

in which X is H, CN, $C(NH)NH_2$, $C(O)NH_2$, $C(NH)NHCN$, or a condensation product thereof;
a is 1, 2, 3, 4, 5 or 6;
each M is independently Ca, Mg, Zn or Al;
m is 2 or 3;
b is 1, 2, 3, 4 or 5;
C is 0, 1, 2 or 3;
d is 1, 2 or 3, and
where: $a+b*m=(5+c)*d$,
or a coordination polymer of the compound of the formula (I).

The object is additionally achieved by a polymer obtainable from the water-eliminating polycondensation of a monomeric compound of the formula (II)

$$[(A-H)^+]_2 \left[ \text{structure} \right] \quad (II)$$

where
$(A-H)^+$ and c are each as defined above, or a salt thereof.

The object is further achieved by a compound of the formula (III-1) or of the formula (III-2)

$$[(A-H)^+]_m [M^{m+}(HPO_4^{2-})_m] \quad (III-1)$$

$$[(A-H)^+]_m [M^{m+}(P_2O_7^{4-})_{m/2}] \quad (III-2)$$

where
$(A-H)^+$, M and m are each as defined above.

In compounds of the formulae (I), (II) and (III), a $[(A-H)^+]$ radical occurs, which corresponds to the formula (IV) and is ionic in nature. The deprotonated base form corresponds to melamine when X=H. The radicals are introduced into compounds of the formulae (I), (II) and (III) according to their base forms. In this context, they themselves or condensation products thereof may be used with elimination of ammonia. In the case of melamine, these are, for example, melam, melem or melon. Preferably, X=H.

Compounds of the formulae (I) and (II) additionally derive from aminomethanephosphonic acids and may contain ethyleneammonium units (c is not zero). Such compounds can be prepared in a simple manner from ethylenediamine, formaldehyde and phosphorous acid or phosphites. Such a preparation is described, for example, in J. Org. Chem. (1966), 1603-1607.

Preferably, c in the above formulae is 0 or 1.

The compounds of the formula (I) can be used as such, or they are converted thermally to coordination polymers thereof. In this case, there is a bridging coordinate bond of a phosphorous-containing anionic ligand to two different metal cations, such that a polymeric coordination framework can be formed.

Compounds of the formulae (I) and (III) contain metal ions, which are preferably Mg or Al.

Compounds of the formula (II) are polymers which can be obtained by simple thermal dehydration from monomers known per se, or are salts thereof, in which remaining OH groups form salts when deprotonated with cations. The cations are preferably those of the formula $(A-H)^+$, especially melaminium.

The chemical formulae shown above are limiting formulae which represent the radicals in the ionic state. However, this need not correspond to the actual charge distribution. In addition, tautomeric forms of the structures shown above may also occur and are also included in the scope of the present invention.

Figure 1:
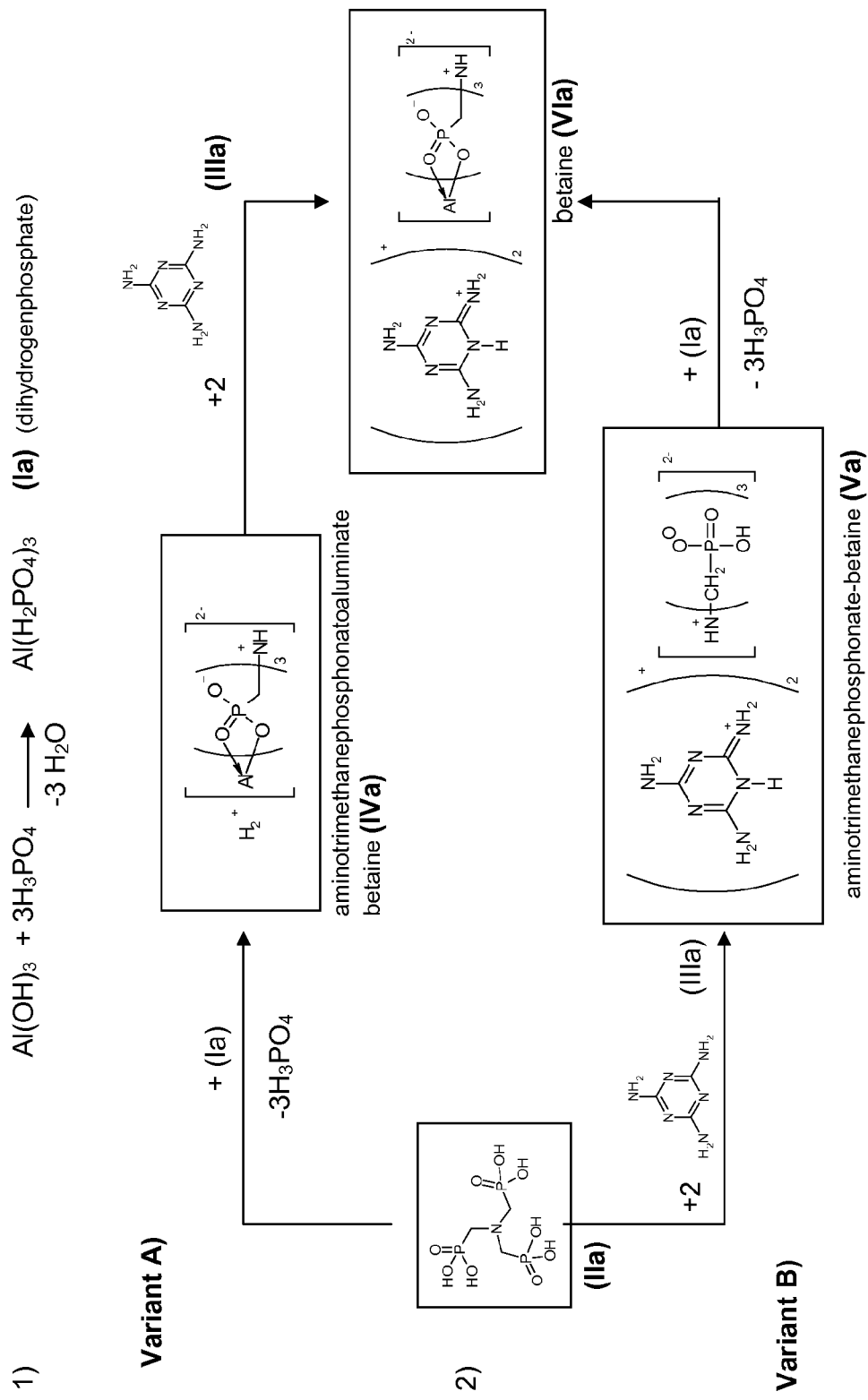
FIG. 1 illustrates reactions for the preparation of compounds of formula I.

Examples of the novel compounds of the formula (I) are the following compounds, where Mel represents melamine.

a) Derivatives of nitrilotrismethanephosphonic acid ($H_6$-NTPMA, c=0):

$$[(Mel-H)^+]_3[Mg(HNTMPA)]^{3-} \quad (1)$$

$$[(Mel-H)^+]_2[Al(HNTMPA)]^{2-} \quad (2)$$

$$[(Mel-H)^+]_4[Mg_3(HNTMPA)_2]^{4-} \quad (3)$$

$$[(Mel-H)^+]_4[Ca_3(HNTMPA)_2]^{4-} \quad (4)$$

$$[(Mel-H)^+]_4[Zn_3(HNTMPA)_2]^{4-} \quad (5)$$

$$[(Mel-H)^+]_3[Mg_2Al(HNTMPA)_2]^{3-} \quad (6)$$

$$[(Mel-H)^+]_2[MgAl_2(HNTMPA)_2]^{2-} \quad (7)$$

b) Derivatives of ethylenediaminetetrakismethanephosphonic acid ($H_8$-EDTMP, c=1)

$$[(Mel-H)^+]_4[Mg(H_2EDTMP)]^{4-} \quad (8)$$

$$[(Mel-H)^+]_4[Ca(H_2EDTMP)]^{4-} \quad (9)$$

$$[(Mel-H)^+]_4[Zn(H_2EDTMP)]^{4-} \quad (10)$$

$$[(Mel-H)^+]_3[Al(H_2EDTMP)]^{3-} \quad (11)$$

$$[(Mel-H)^+]_2[Mg_2(H_2EDTMP)]^{2-} \quad (12)$$

$$[(Mel-H)^+]_2[Ca_2(H_2EDTMP)]^{2-} \quad (13)$$

$$[(Mel-H)^+]_2[Zn_2(H_2EDTMP)]^{2-} \quad (14)$$

$$[(Mel-H)^+][MgAl(H_2EDTMP)]^- \quad (15)$$

$$[(Mel-H)^+][CaAl(H_2EDTMP)]^- \quad (16)$$

$$[(Mel-H)^+][ZnAl(H_2EDTMP)]^- \quad (17)$$

c) Derivatives of diethylenetriaminepentakismethanephosphonic acid ($H_{10}$-DETPMP, c=2)

$$[(Mel-H)^+]_5[Mg(H_3DETPMP)]^{5-} \quad (18)$$

$$[(Mel-H)^+]_5[Ca(H_3DETPMP)]^{5-} \quad (19)$$

$$[(Mel-H)^+]_5[Zn(H_3DETPMP)]^{5-} \quad (20)$$

$$[(Mel-H)^+]_4[Al(H_3DETPMP)]^{4-} \quad (21)$$

$$[(Mel-H)^+]_3[Mg_2(H_3DETPMP)]^{3-} \quad (22)$$

$$[(Mel-H)^+]_3[Ca_2(H_3DETPMP)]^{3-} \quad (23)$$

$$[(Mel-H)^+]_3[Zn_2(H_3DETPMP)]^{3-} \quad (24)$$

$$[(Mel-H)^+]_2[MgAl(H_3DETPMP)]^{2-} \quad (25)$$

$$[(Mel-H)^+]_2[CaAl(H_3DETPMP)]^{2-} \quad (26)$$

$$[(Mel-H)^+]_2[ZnAl(H_3DETPMP)]^{2-} \quad (27)$$

$$[(Mel-H)^+][Mg_3(H_3DETPMP)]^- \quad (28)$$

$$[(Mel-H)^+][Ca_3(H_3DETPMP)]^- \quad (29)$$

$$[(Mel-H)^+][Zn_3(H_3DETPMP)]^- \quad (30)$$

$$[(Mel-H)^+]_4[Mg_5(H_3DETMP)_2]^{4-} \quad (31)$$

$$[(Mel-H)^+]_4[Ca_5(H_3DETMP)_2]^{4-} \quad (32)$$

$$[(Mel-H)^+]_4[Zn_5(H_3DETMP)_2]^{4-} \quad (33)$$

$$[(Mel-H)^+]_2[Mg_3Al_2(H_3DETMP)_2]^{2-} \quad (34)$$

$$[(Mel-H)^+]_2[Ca_3Al_2(H_3DETMP)_2]^{2-} \quad (35)$$

$$[(Mel-H)^+]_2[Zn_3Al_2(H_3DETMP)_2]^{2-} \quad (36)$$

d) Derivatives of triethylenetetraminehexakismethanephosphonic acid ($H_{12}$-TETHMP, c=3)

$$[(Mel-H)^+]_6[Mg(H_4TETHMP)]^{6-} \quad (37)$$

$$[(Mel-H)^+]_6[Ca(H_4TETHMP)]^{6-} \quad (38)$$

$$[(Mel-H)^+]_6[Zn(H_4TETHMP)]^{6-} \quad (39)$$

$$[(Mel-H)^+]_5[Al(H_4TETHMP)]^{5-} \quad (40)$$

$$[(Mel-H)^+]_4[Mg_2(H_4TETHMP)]^{4-} \quad (41)$$

$$[(Mel-H)^+]_4[Ca_2(H_4TETHMP)]^{4-} \quad (42)$$

$$[(Mel-H)^+]_4[Zn_2(H_4TETHMP)]^{4-} \quad (43)$$

$$[(Mel-H)^+]_2[Al_2(H_4TETHMP)]^{2-} \quad (44)$$

$$[(Mel-H)^+]_2[Mg_3(H_4TETHMP)]^{2-} \quad (45)$$

$$[(Mel-H)^+]_2[Ca_3(H_4TETHMP)]^{2-} \quad (46)$$

$$[(Mel-H)^+]_2[Zn_3(H_4TETHMP)]^{2-} \quad (47)$$

$$[(Mel-H)^+]_3[MgAl(H_4TETHMP)]^{3-} \quad (48)$$

$$[(Mel-H)^+]_3[CaAl(H_4TETHMP)]^{3-} \quad (49)$$

$$[(Mel-H)^+]_3[ZnAl(H_4TETHMP)]^{3-} \quad (50)$$

$$[(Mel-H)^+][Mg_2Al(H_4TETHMP)]^- \quad (51)$$

$$[(Mel-H)^+][Ca_2Al(H_4TETHMP)]^- \quad (52)$$

$$[(Mel-H)^+][Zn_2Al(H_4TETHMP)]^- \quad (53)$$

Figure 2:
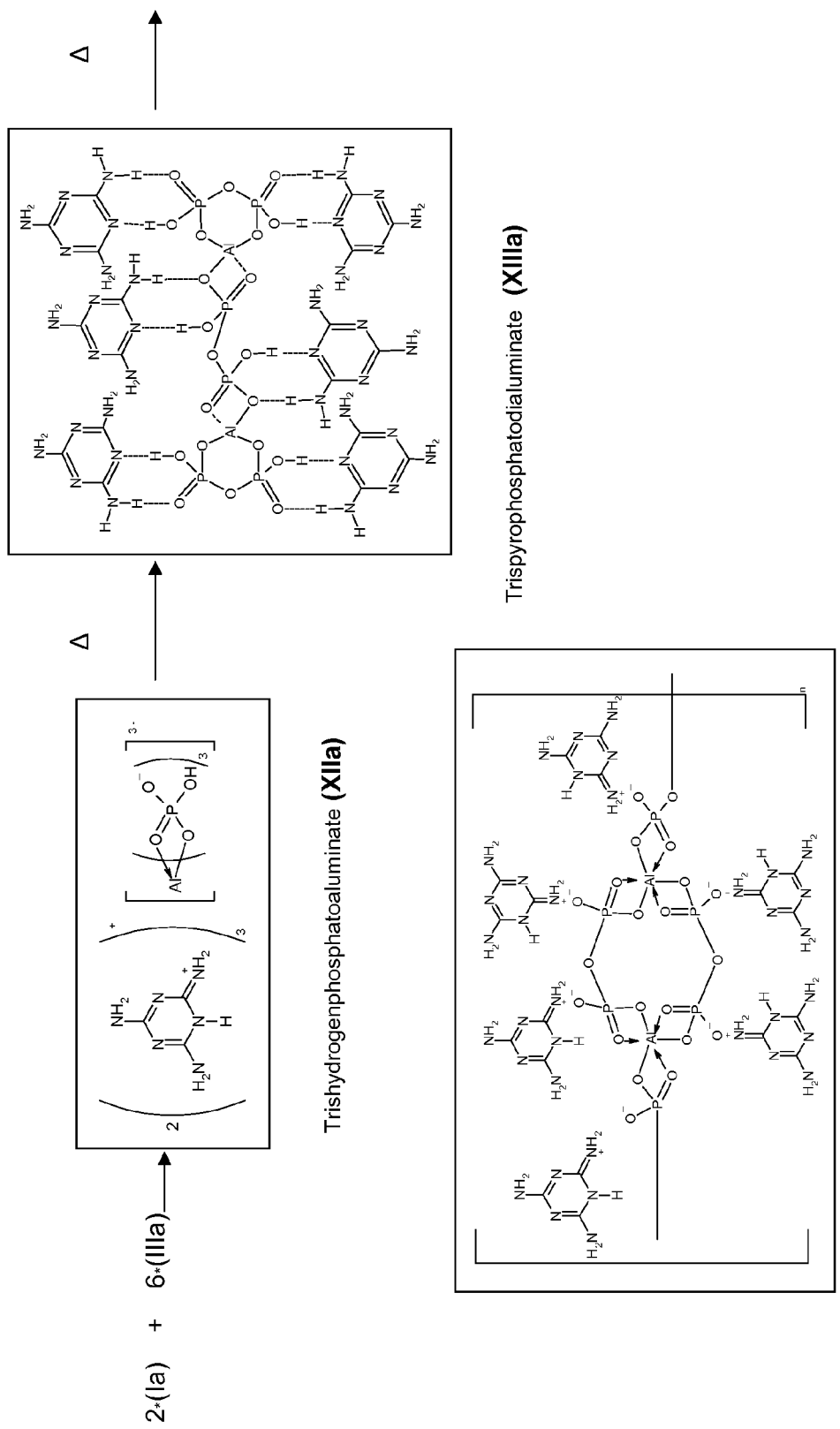
FIG. 2 illustrates coordination polymers prepared with compounds of formula I.

Such compounds are generally obtainable by the reactions shown in FIG. 1. Illustrative coordination polymers are shown in FIG. 2.

Compounds of the formula (II) are, for example, the following derivatives. It is preferred here that the polymers are formed from 2, 3, 4, 5 or 6 monomers. Compounds (54) to (57) are salts in which only some of the OH groups form an —O— bridge with elimination of water and the rest of the OH groups form the corresponding melaminium salts with melamine.

Pyroaminomethanephosphonic acid derivatives:

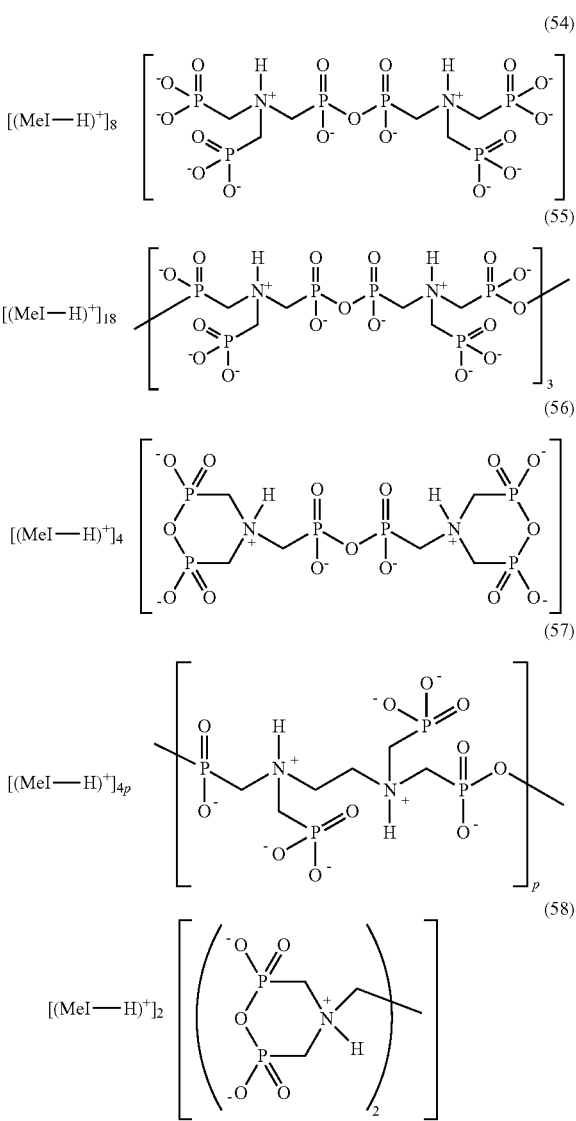

Figure 3:
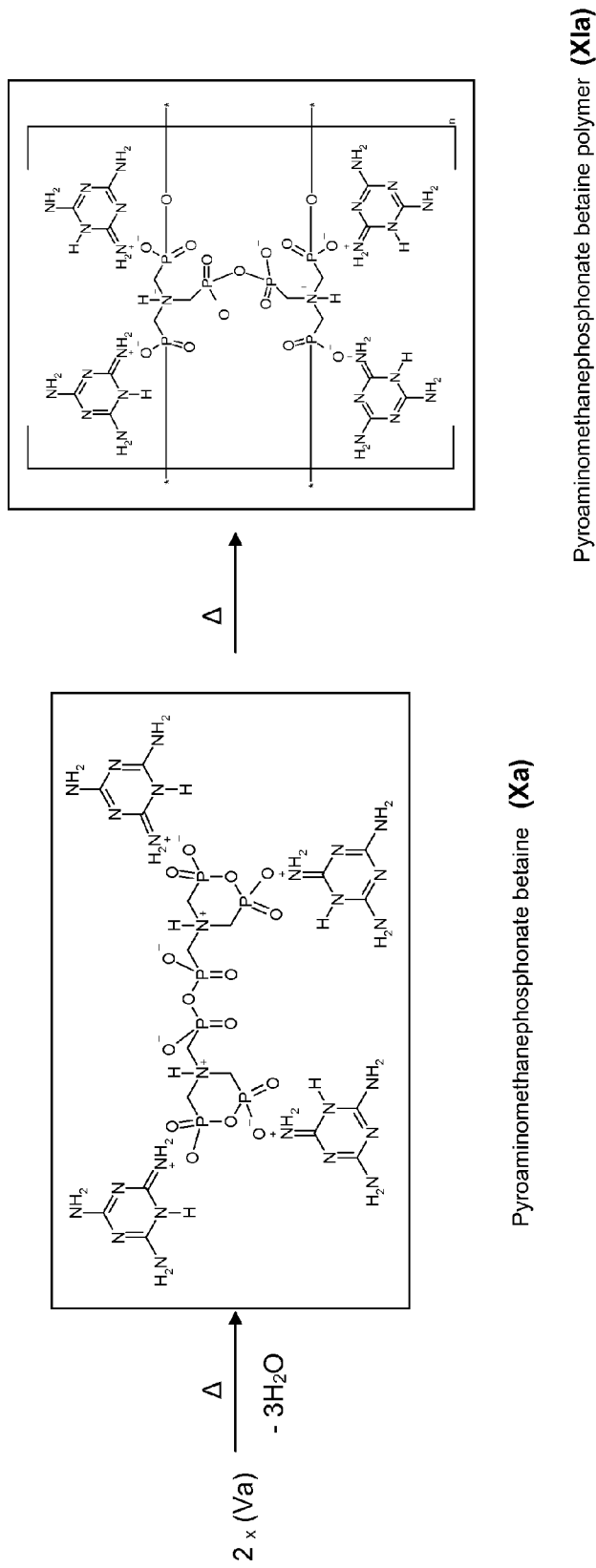
FIG. 3 illustrates reactions for the preparation of polymers prepared from compounds of formula II.
Figure 4:
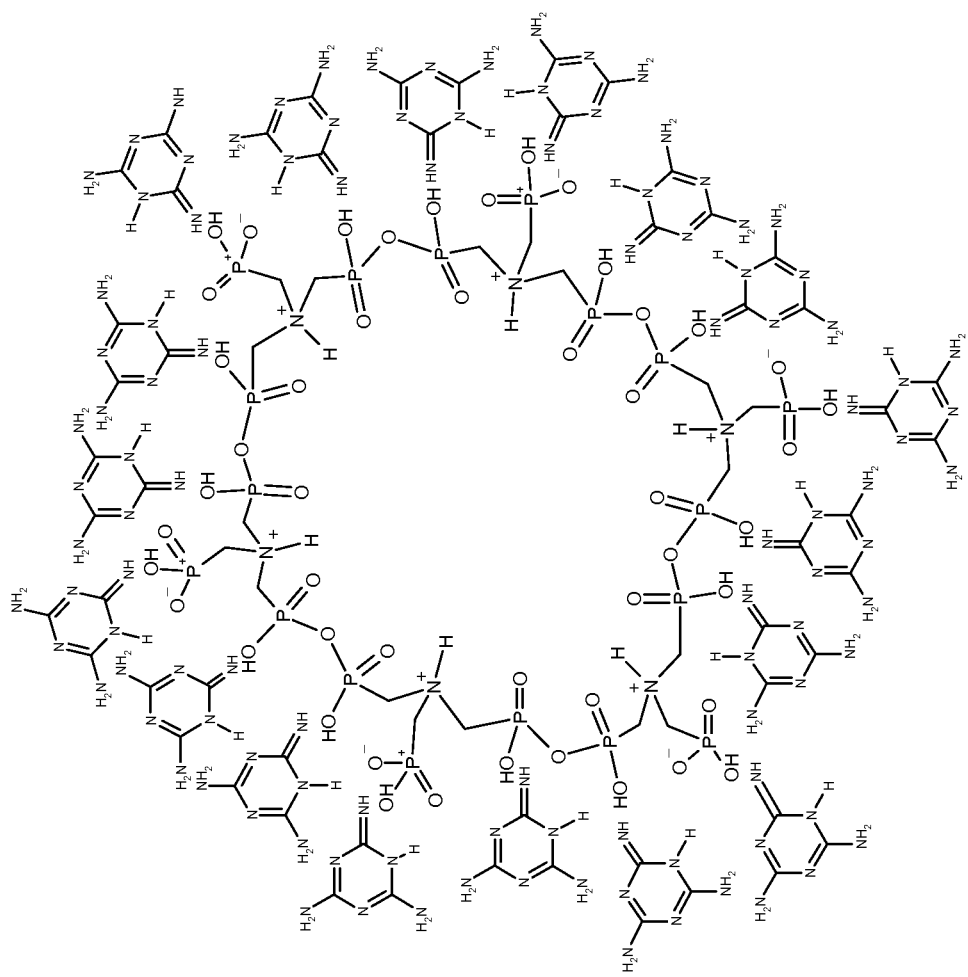
FIG. 4 illustrates a polymer prepared from compounds of formula II.

Further polymers proceeding from compounds of the formula (II) and reactions to prepare such polymers are shown in FIG. 3 and FIG. 4.

Examples of compounds of the formula (III) are the following compounds:

Preference is given to: 1, 2, 8, 11, 12, 15, 54, 55, 56, 57, 58, 59, 62, 63 and 66.

Particular preference is given to: 1, 2, 8, 11, 54, 55 and 56.

Very particular preference is given to: 54, 55 and 56.

Compounds 1 to 53 (category a) are metallaminophosphonates with complex anions which contain at least one tetra- or hexavalent metal atom (Mg, Ca, Zn, Al) as a coordination center with bidentate (bipodal) phosphonate ligands, and at least one ternary ammonium-phosphonate-betaine structure (internal phosphonate) in the molecule.

Compounds 59 to 66 (category b) represent hydrogenphosphato- or pyrophosphatometallates with complex anions, which have a tetra- or hexavalent metal atom (Mg, Ca, Zn, Al) as a coordination center with bidentate hydrogen phosphate or pyrophosphate ligands.

Compounds 54 to 58 (category c) contain pyroaminomethanephosphonate anions with ternary ammonium-phosphonate-betaine structures.

The compounds of category a) can be synthesized according to variant A) or B) as per FIG. 1.

In variant A), the first stage involves conversion to the $M(H_2PO_4)_{2\ or\ 3}$ solution (Ia), preceding from stoichiometric amounts of conc. $H_3PO_4$ and $MtO/Mt_2O_3$, $Mt(OH)_{2\ or\ 3}$ or $MtCO_3$, which goes completely into solution (see Example 1).

In stage 2), the aqueous solution thus obtained is reacted with molar amounts of aqueous aminomethanephosphonic acid solution, which precipitates a white solid, which is filtered, washed and dried (IVa, see Example 2). The phosphoric acid released (or concentrated solution thereof) can be recovered by concentrating the filtrate and be returned to the reaction cycle.

In stage 3), (IVa) is initially charged, preferably in aqueous suspension at 50-60° C., and melamine (Ma) is added in portions. The voluminous end product (VIa) is filtered off with suction, washed and dried (see Example 5).

Heat treatment at 240° C. for several hours forms a coordination polymer (VIIa).

In variant B), the first stage involves a partial conversion to the melamine aminomethanephosphonate (Va), which is filtered, washed and dried (see Example 3). In stage 2), (Va) is reacted with (Ia), preference being given to initially charging (Ia) and adding (Va) in portions at 50-60° C. The voluminous end product (VIa) is filtered off with suction, washed and dried (see Example 5).

Heat treatment at 240° C. for several hours forms a coordination polymer (not shown in FIG. 1).

Both variants afford virtually quantitative yields of (VIa).

Variant B) is preferred.

The compounds according to category a) are synthesized according to FIGS. 1 and 2.

According to Example 1, reaction is effected with $H_3PO_4$ to give the aqueous $Mt(H_2PO_4)_2$ or 3 solution which is subsequently homogenized with solid melamine (IIIa). Alternatively, the aqueous solution can be sprayed onto melamine, which forms the monomer (XIIa)—see Example 6.

Heat treatment at 240° C. for several hours affords oligomeric or polymeric pyrophosphato-dialuminates (XIIIa and XIVa).

Preference is given to a spraying process.

The compounds according to category c) are synthesized according to FIGS. 1 and 3. Partial aminomethanephosphonates (Va)—see Example 3—are converted by heating to 220° C. for several hours to monomeric pyroaminomethanephosphonates (Xa), from which, thereafter, polymeric pyroaminomethanephosphonates (XIa) form by heat treatment at 250-260° C. (see Example 4).

The inventive flame retardants are highly suitable for imparting flame retardancy properties to synthetic polymers, especially thermoplastic polymers.

The present invention provides for the use of an inventive compound as a flame retardant in a polymer, preferably a thermoplastic, especially a polyamide, polyurethane, polystyrene, polyolefin or polyester, or a thermoset, especially epoxy resin.

Accordingly, the present invention further provides a polymer containing an inventive compound. It will be appreciated that it is also possible to use a plurality of inventive compounds.

In addition, the polymer may contain further compounds other than the inventive compounds. Examples here include melamine, melaminium phosphate or melamine cyanurate.

A preferred embodiment of the present invention therefore relates to a polymer additionally containing at least one of the compounds selected from the group consisting of melamine, melaminium phosphate and melamine cyanurate.

Examples of such synthetic polymers are:

1. Polymers of mono- and diolefins, for example polypropylene, polyisobutylene, polybutene-1, poly-4-methylpentene-1, polyvinylcyclohexane, polyisoprene or polybutadiene, and polymers of cycloolefins, for example of cyclopentene or norbornene and polyethylene (including crosslinked), for example High Density Polyethylene (HDPE) or High Molecular Weight (HDPE-HMW), High Density Polyethylene with Ultra-High Molecular Weight (HDPE-UHMW), Medium Density Polyethylene (MDPE), Low Density Polyethylene (LDPE) and Linear Low Density Polyethylene (LLDPE), (VLDPE) and (ULDPE).
2. Polystyrenes, poly(p-methylstyrene), poly($\alpha$-methylstyrene).
3. Copolymers and graft copolymers of polybutadiene-styrene or polybutadiene and (meth)acrylonitrile, for example ABS and MBS.
4. Halogenated polymers, for example polychloroprene, polyvinyl chloride (PVC), polyvinylidene chloride (PVDC), copolymers of vinyl chloride/vinylidene chloride, vinyl chloride/vinyl acetate or vinyl chloride/vinyl acetate.
5. Poly(meth)acrylates, polymethyl methacrylates (PMMA), polyacrylamide and polyacrylonitrile (PAN).
6. Polymers of unsaturated alcohols and amines or acyl derivatives or acetals thereof, for example polyvinyl alcohol (PVA), polyvinyl acetates, stearates, benzoates or maleates, polyvinyl butyral, polyallyl phthalates and polyallylmelamines.
7. Homo- and copolymers of cyclic ethers, such as polyalkylene glycols, polyethylene oxides, polypropylene oxides and copolymers thereof with bisglycidyl ethers.
8. Polyacetals such as polyoxymethylenes (POM), and polyurethane- and acrylate-modified polyacetals.
9. Polyphenylene oxides and sulfides, and mixtures thereof with styrene polymers or polyamides.
10. Polyamides and copolyamides derived from diamines and dicarboxylic acids and/or from aminocarboxylic acids or the corresponding lactams, for example nylon 4, nylon 6, nylon 6/6, 6/10, 6/9, 6/12, 12/12, nylon 11, nylon 12, aromatic polyamides derived from m-xylylenediamine and adipic acid, and copolyamides modified with EPDM or ABS. Examples of polyamides and copolyamides are derived from 8-caprolactam, adipic acid, sebacic acid, dodecanoic acid, isophthalic acid, terephthalic acid, hexamethylenediamine, tetramethylenediamine, 2-methylpentamethylenediamine, 2,2,4-trimethylhexamethylenediamine, 2,4,4-trimethylhexamethylenediamine, m-xylylenediamine or bis(3-methyl-4-aminocyclohexyl)methane.
11. Polyureas, polyimides, polyamideimides, polyetherimides, polyesterimides, polyhydantoins and polybenzimidazoles.
12. Polyesters derived from dicarboxylic acids and dialcohols and/or hydroxycarboxylic acids or the corresponding lactones, for example polyethylene terephthalate, polypropylene terephthalate, polybutylene terephthalate, poly-1,4-dimethylcyclohexane terephthalate, polyalkylene naphthalate (PAN) and polyhydroxybenzoates, polylactic esters and polyglycolic esters.
13. Polycarbonates and polyester carbonates.
14. Polyketones.
15. Mixtures or alloys of the abovementioned polymers, e.g. PP/EPDM, PA/EPDM or ABS, PVC/EVA, PVC/ABS, PBC/MBS, PC/ABS, PBTP/ABS, PC/AS, PC/PBT, PVC/CPE, PVC/acrylate, POM/thermoplastic PU, PC/thermoplastic PU, POM/acrylate, POM/MBS, PPO/HIPS, PPO/N6,6 and copolymers, PA/HDPE, PA/PP, PA/PPO, PBT/PC/ABS or PBT/PET/PC.
16. Thermosets such as PF, MF or UF or mixtures thereof
17. Epoxy resins—thermoplastics and thermosets
18. Phenoxy resins.
19. Wood-plastic composites (WPC)

The concentration of the claimed flame retardant in the polymer is preferably 0.1 to 60% by weight based on the polymer to be processed.

The flame retardant can be prepared by compounding (in apparatus such as a twin-screw extruder, for example by premixing in the form of powder and/or granule in a mixer and then by homogenizing in a polymer melt. The flame retardant can possibly also be added directly in the course of processing.

The material thus rendered flame-retardant can be processed to fibers, films, cast articles, and be used for treatment of surfaces.

The flame retardant can also be used for surface treatment (impregnation) of fibers, films, textiles or other industrial materials.

Coating of metal surfaces can also achieve an anticorrosive protective effect.

The inventive polymer preparations can be provided with further known synergists and co-components such as aryl or chloroalkyl phosphates, arylene diphosphates, bisphenol A (F) diphosphates, polymeric aryl phosphates, bisazinepentaerythrityl diphosphate salts, hexa-aryloxytriphosphazenes, polyaryloxyphosphazenes and siloxanes ($R_2SiO$)$_r$ or ($RSiO_{1.5}$)$_r$, especially POSS compounds (Polyhedral Oligomeric SilSesquioxanes), and metal phosphinates or metal hypophosphites (metal: Mg, Ca, Zn and Al), or the char formers such as pentaerythritol, dipentaerythritol and tripentaerythritol or esters thereof, or promoters therefor.

The following additives should additionally be mentioned: Metal hydroxides, for example aluminum or magnesium hydroxide,
metal borates, for example calcium, magnesium, manganese or zinc borates, metal oxides such as magnesium, aluminum, manganese, zinc and antimony oxide or titanium dioxide, silicon dioxide; metal phosphates, for example magnesium, calcium, zinc and aluminum phosphate; clay minerals such as kaolinite, muscovite, pyrophyllite, bentonite and talc, or other minerals such as wollastonite, quartz, mica, feldspar or mineral anion exchangers such as hydrotalcites or other magnesium-aluminum hydroxocarbonates or calcium-aluminum hydroxocarbonates.

Foam formers include: melamine, melamine-formaldehyde resins, melamine cyanurate, melamine polyphosphate; urea derivatives such as urea, thiourea, guanamines, benzoguanamine, acetoguanamine and succinylguanamine, dicyandiamide, guanidine and guanidine sulfamate and other guanidine salts, or allantoins, glycolurils and trishydroxyethyl isocyanurate.

The inventive polymer preparations may additionally comprise antidripping agents, especially based on polytetrafluoroethylene. The concentration of such antidripping agents is 0.01 to 15% by weight, based on the polymer to be processed.

In addition, further components can be added to the formulations, for example fillers and reinforcing agents, such as glass fibers, glass beads or mineral additives such as chalk. As further additives may antioxidants, light stabilizers, lubricants, pigments, nucleating agents and antistats.

EXAMPLES

Example 1

Precursor

Preparation of aluminum trisdihydrogenphosphate (Ia): 23.4 g (0.3 mol, moist) of aluminum hydroxide are dissolved in 88.2 g (0.9 mol, 85%) phosphoric acid while stirring and heating.

Example 2

Precursor

Preparation of (IVa): to the solution of (Ia), prepared according to Example 1, are added gradually 89.7 g (0.3 mol) of aminotrimethanephosphonic acid (IIa) (Dequest 2000, 50% solution from SOLUTIA). The precipitated white solid is filtered off, washed and dried to constant weight (dihydrogenaminotrimethanephosphonatoaluminate betaine (IVa)).

Yield: 87 g (approx. 90% of theory); m.p.: >300° C.

Example 3

Precursor

Preparation of bismelaminium trihydrogenaminotrimethanephosphonate betaine (Va): to an aqueous solution containing 89.7 g (0.3 mol) of aminotrimethanephosphonic acid (IIa) (Dequest 2000, 50% solution from SOLUTIA) are added 75.7 g (0.6 mol) of melamine (Ma) in portions while stirring and heating. After a few minutes, a voluminous white precipitate forms, which is filtered off with suction and dried to constant weight.

Yield: 155 g (approx. 94% of theory); m.p.: >300° C.

Example 4

Inventive

By heating (Va) to 200-220° C., it is possible to obtain the pyroaminomethanephosphonate betaine (Xa), from which polymeric pyroaminomethanephosphonate betaine (XIa) forms by heating at 230-250° C. for several hours.

Example 5

Inventive

Preparation of bismelaminium hydrogenaminotrimethanephosphonatoaluminate betaine (VIa)
Variant A: (IVa)+(IIIa)

32.3 g (0.1 mol) of (IVa) are suspended in 800 ml of water and heated to 50-60° C. while stirring. To this suspension are added 25.3 g (0.2 mol) of melamine (IIIa) in portions. Within a few minutes, a voluminous white precipitate forms, which is filtered off with suction and dried to constant weight.

Yield: 52.0 g (approx. 90% of theory); m.p.: >250° C.
Variant B: (Ia)+(Va)

A solution of 0.15 mol of (Ia), prepared according to Example 1, is initially charged in 800 ml of water and heated to 50-60° C. while stirring. To this solution are added 82.7 g (0.15 mol) of (Va) in portions. After about 4 hours, a voluminous product forms, which is filtered off with suction and dried to constant weight.

Yield: 78.0 g (approx. 90% of theory); m.p.: >300° C.

Both products can be converted to a coordination polymer (VIIa) by heating at 230-250° C. for several hours.

Example 6

Inventive

Preparation of trismelaminium trishydrogenphosphatoaluminate (XIIa)

An aqueous solution of 318.0 g (1.0 mol) of (Ia) is sprayed onto 378.4 g (3.0 mol) of melamine (Ma). After drying, the product yield is virtually quantitative; m.p.: >300° C. Heating at 230-250° C. for several hours forms hexamelaminium trispyrophosphatodialuminate (XIIIa), which is converted by further heating to polyhexamelaminium bispyrophosphatophosphatodialuminate (XIVa).

The invention claimed is:

1. A compound of the formula (III-1) or of the formula (III-2)

 (III-1)

 (III-2)

where
(A-H)$^+$ is a radical of the formula (IV)

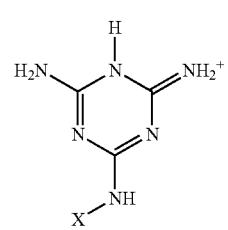 (IV)

in which X is H, CN, C(NH)NH$_2$, C(O)NH$_2$, C(NH)NHCN, or a condensation product thereof;
each M is independently Ca, Mg, Zn or Al; and
m is 2 or 3,
characterized in that the molar ratio of (A-H)$^+$ to phosphorus is less than 1.1.

2. A compound as claimed in claim 1, characterized in that M is Mg or Al.

3. A compound as claimed in claim 1, characterized in that X in formula (IV) is H.

4. A compound of the formula (III) according to claim 1, selected from the group consisting of

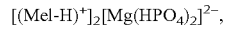

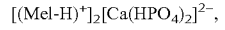

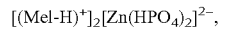

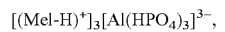

$[(Mel-H)^+]_2[MgP_2O_7]^{2-}$, $[(Mel-H)^+]_2[CaP_2O_7]^{2-}$, $[(Mel-H)^+]_2[ZnP_2O_7]^{2-}$ and $[(Mel-H)^+]_3[Al(P_2O_7)_{3/2}]^{3-}$.

5. Method of using a compound as claimed in claim 1 as a flame retardant in a polymer.

6. The method as claimed in claim 5, characterized in that the polymer is a thermoplastic or thermoset.

7. The method as claimed in claim 6, characterized in that the thermoplastic is a polyamide, polyurethane, polystyrene, polyolefin or polyester, and the thermoset is an epoxy resin.

8. A polymer containing a compound as claimed in claim 1.

9. A polymer as claimed in claim 8, additionally containing at least one of the compounds selected from the group consisting of melamine, melaminium phosphate and melamine cyanurate.

\* \* \* \* \*